United States Patent
Edmonson et al.

(10) Patent No.: US 7,053,524 B2
(45) Date of Patent: May 30, 2006

(54) SURFACE ACOUSTIC WAVE SENSOR OR IDENTIFICATION DEVICE WITH BIOSENSING CAPABILITY

(75) Inventors: Peter J. Edmonson, Hamilton (CA); Colin K. Campbell, Ancaster (CA); William D. Hunt, Decatur, GA (US)

(73) Assignee: P.J. Edmonson Ltd., Hamilton (CA)

( * ) Notice: Subject to any disclaimer, the term of this patent is extended or adjusted under 35 U.S.C. 154(b) by 0 days.

(21) Appl. No.: 11/139,477

(22) Filed: May 31, 2005

(65) Prior Publication Data
US 2006/0000285 A1    Jan. 5, 2006

Related U.S. Application Data

(63) Continuation-in-part of application No. 10/729,920, filed on Dec. 9, 2003, now Pat. No. 6,967,428.

(51) Int. Cl.
*G01S 13/80* (2006.01)
*H04Q 5/22* (2006.01)

(52) U.S. Cl. .................. 310/313 D; 342/51; 333/153; 333/154; 340/571.2; 340/825.34

(58) Field of Classification Search .................. None
See application file for complete search history.

(56) References Cited

U.S. PATENT DOCUMENTS

| | | | |
|---|---|---|---|
| 4,088,696 A * | 5/1978 | Schreiber et al. | 568/450 |
| 4,361,026 A * | 11/1982 | Muller et al. | 73/24.01 |
| 4,378,168 A * | 3/1983 | Kuisma et al. | 374/28 |
| 5,966,008 A * | 10/1999 | Maier et al. | 324/96 |
| 6,084,503 A * | 7/2000 | Ruile et al. | 340/10.1 |
| 6,723,516 B1 * | 4/2004 | Tom-Moy et al. | 435/7.1 |
| 6,813,947 B1 * | 11/2004 | Dollinger et al. | 73/432.1 |
| 6,967,428 B1 * | 11/2005 | Edmonson et al. | 310/313 D |
| 2003/0231107 A1 * | 12/2003 | Edmonson et al. | 340/10.42 |

FOREIGN PATENT DOCUMENTS

JP           07260746 A   * 10/1995

* cited by examiner

*Primary Examiner*—Hezron Williams
*Assistant Examiner*—Rose M. Miller
(74) *Attorney, Agent, or Firm*—Robert F. Delbridge

(57) ABSTRACT

A surface acoustic wave sensor or identification device has a piezoelectric material, and an interdigitated transducer (IDT) input/output mounted on the piezoelectric material for receiving a radio frequency (RF) signal and propagating a corresponding surface acoustic wave along a surface of the piezoelectric material. An IDT finger electrode array is mounted on the piezoelectric material and is operable to communicate with the IDT input/output for transmission of a modified RF signal from the device. The IDT finger electrode array has at least one finger electrode segment whose propagating characteristics are controlled to control the nature of the modified RF signal. A biolayer is mounted on the piezoelectric material and is associated with the finger electrode segment, and a fluidic chamber is associated with the biolayer. In use, the fluidic chamber contains fluid which, if a predetermined substance to be sensed or detected is present, operates to modify the biolayer which in turn controls the nature of the modified RF signal.

10 Claims, 4 Drawing Sheets

SURFACE ACOUSTIC WAVE SENSOR OR IDENTIFICATION DEVICE WITH BIOSENSING CAPABILITY

RELATED APPLICATION

This application is a continuation-in-part of U.S. patent application Ser. No. 10/729,920 filed Dec. 9, 2003, now U.S. Pat. No. 6,967,428 the contents of which are hereby incorporated herein by reference.

FIELD OF INVENTION

This invention relates to surface acoustic wave sensors or identification devices with biosensing capability.

BACKGROUND OF INVENTION

The invention described and claimed in parent application Ser. No. 10/729,920 provides a surface acoustic wave sensor or identification device having a piezoelectric substrate, an interdigitated transducer (IDT) input/output mounted on the substrate for receiving a radio frequency (RF) signal and propagating a corresponding surface acoustic wave along a surface of the substrate, and an IDT reflector array mounted on the substrate and operable to receive the surface acoustic wave and reflect the surface acoustic wave in modified form back to the IDT input/output for transmission of a corresponding modified RF signal from the device. The IDT reflector array has at least one reflector sector whose reflectivity characteristics are controlled to control the nature of the modified RF signal. The device also includes at least one reflector segment having a fluidic chamber which in use contains fluid operable to control the nature of the reflected surface acoustic wave and hence the nature of the modified RF signal.

It is an object of the present invention to provide a surface acoustic wave sensor or identification device of this kind which has a biolayer which is modified by the fluid in the fluidic chamber.

SUMMARY OF INVENTION

According to the present invention, a surface acoustic wave sensor or identification device has a piezoelectric material, an interdigitated transducer (IDT) input/output mounted on the piezoelectric material for receiving a radio frequency (RF) signal and propagating a corresponding acoustic wave along a surface of the piezoelectric material, an IDT finger electrode array mounted on the piezoelectric material and operable to communicate with the IDT input/output for transmission of a modified RF signal from the device, the IDT finger electrode array having at least one finger electrode segment whose propagating characteristics are controlled to control the nature of the modified RF signal, a biolayer mounted on the piezoelectric material and associated with the finger electrode segment, and a fluidic chamber associated with the biolayer and which in use contains fluid which, if a predetermined substance to be sensed or identified is present, operates to modify the biolayer which in turn controls the nature of the modified RF signal.

The acoustic wave generated by the IDT may be any one of the recognized types, for example Rayleigh, Surface Transverse Wave, etc. Also, in this application, the term "fluid" follows the accepted definition which, when taken in its broadest sense, includes materials in either the liquid or gaseous phase.

The IDT finger electrode array may comprise a reflector array or may comprise a modulated IDT array.

The fluidic chamber may have an inlet and an outlet whereby in use fluid flows through the chamber from the inlet to the outlet.

The at least one finger electrode segment may have at least one pair of interdigitated fingers which communicate with the fluidic chamber. The at least one pair of interdigitated fingers may project into the chamber.

DESCRIPTION OF THE DRAWINGS

Embodiments of the invention will now be described by way of example, with reference to the accompanying drawings, of which.

DESCRIPTION OF PREFERRED EMBODIMENTS

Figure 1:
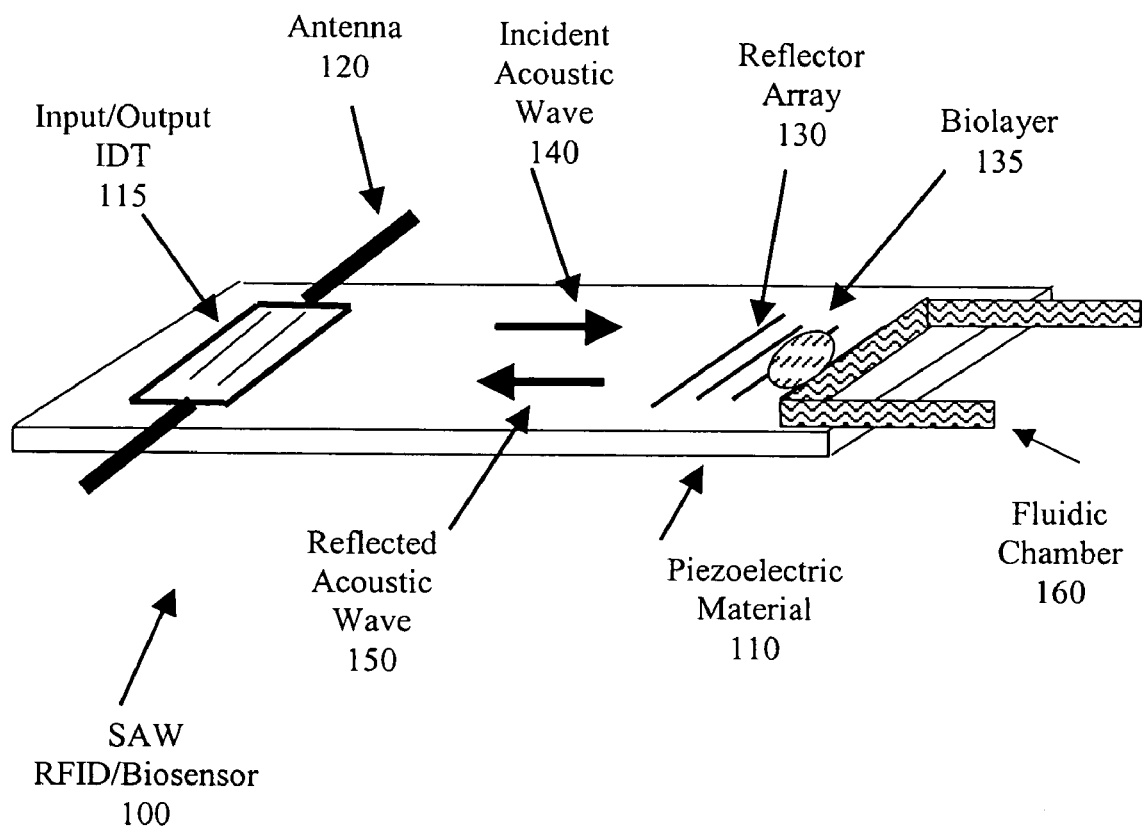
FIG. 1 is a schematic perspective view of a SAW RFID biosensor device in accordance with one embodiment of the invention.

Referring first to FIG. 1 of the drawings, a SAW RFID biosensor system comprises a main interrogation unit (not shown) which transmits an RF signal to a passive SAW sensor 100 located a short distance away. The SAW reflective RFID biosensor 100 receives the RF interrogation signal from the main interrogation unit via an antenna 120 which is electrically connected to an interdigital transducer (IDT) 115 located on piezoelectric material 110. The RF interrogation signal is transformed by the IDT 115 to an incident acoustic wave 140 which propagates towards a reflector array 130 which has several finger electrodes. A biolayer 135 is positioned on or near certain reflectors within the reflector array 130. The biolayer 135 (e.g. antibody, cell or enzyme) is immobilized unto certain reflectors of the reflector array 130 as the target-sensitive component of the biosensor.

Recent literature by Hunt et al., ("Time-dependent signatures of acoustic wave biosensors," *IEEE Proceedings*, Vol. 91, no. 6, pp. 890–901, June 2003.) and (Stubbs, D. D., Lee, S. H. and Hunt, W. D., "Investigation of cocaine plumes using surface acoustic wave immunosassay sensors," *Analytical Chemistry*, vol. 75, no. 22, pp. 6231–6235, Nov. 15, 2003) has demonstrated that an acoustic wave biosensor with an immobilized biolayer need not be restricted to the detection of biomolecules within a liquid phase, but can detect low vapour pressure chemical molecules such as pathogens, drugs and explosives.

The reflector array 130 returns a reflected acoustic wave 150 in the form of a modified interrogation signal such that the modification of the RF signal is proportional to the binding of biological and chemical substances to the biolayer 135. A fluidic chamber 160 enables biological and chemical fluid therein to interact with the biolayer 135. The modified reflected acoustic wave 150 is then reconverted back within the IDT 115 to a modified RF signal which is retransmitted back via the antenna 120 to the interrogation unit.

Figure 2:
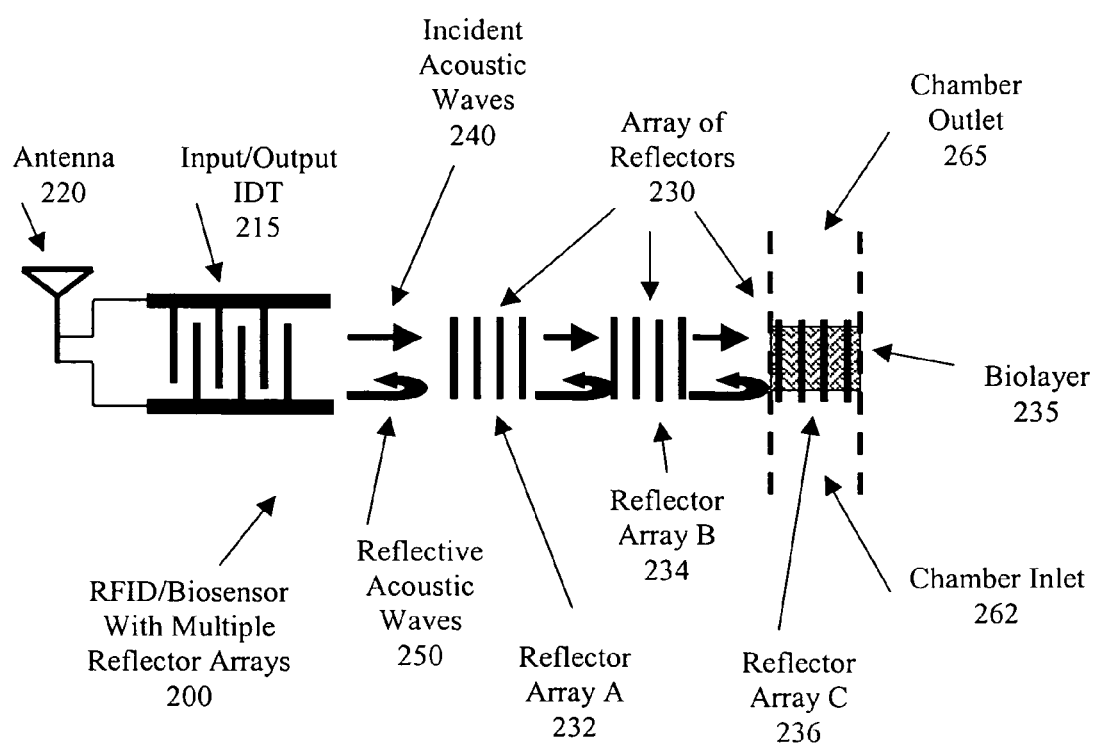
FIG. 2 is a schematic view of a SAW RFID biosensor with multiple reflector arrays in accordance with another embodiment.

FIG. 2 shows an RFID biosensor with multiple reflector arrays 200. The biosensor of FIG. 2 is similar to the RFID biosensor 100 of FIG. 1 in that the antenna 220 receives an interrogation signal which is converted to an incident acoustic wave 240 by the input/output IDT 215. However, reflector array A 232 does not have a biolayer affixed thereto and is suitably positioned away from the input/output IDT 215 such that an unperturbed reflected wave 250 returning back to the input/output IDT 215 from the reflector array A 232 provides a fixed reference signal to a detection algorithm within the main interrogation unit. Similarly, a reflector array B 234 also provides an unperturbed reference signal. A reflector array C 236 does have a biolayer 235 positioned on or near its reflectors and the reflected acoustic wave 250 is perturbed proportionally to the binding effect of the biological and chemical substances to the biolayer 235. A fluidic chamber inlet 262 enables the biological and chemical fluid to enter the fluidic chamber and interact with the biolayer 235, and a fluidic chamber outlet 265 permits exit of the fluid from the fluidic chamber.

The main interrogation unit now has two reference signals followed by a perturbed signal returning from the RFID biosensor. The detection algorithm located within the main interrogation unit can deduce, by comparison techniques between the reference signals and the perturbed signal from reflector C 236, binding events which occurred within the biolayer 235.

Figure 3:
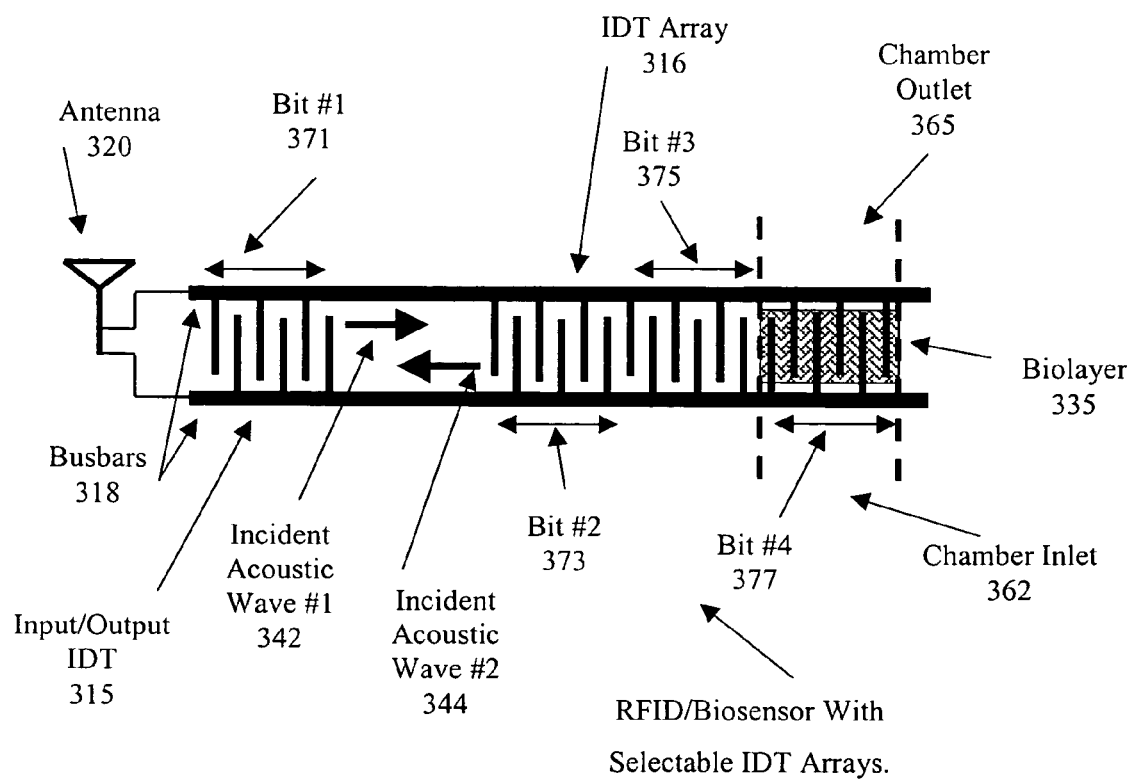
FIG. 3 is a similar view of an RFID biosensor with selectable IDT arrays in accordance with a further embodiment.

A similar approach to selectable reflector arrays is to implement a SAW RFID biosensor with selectable IDT array 300. FIG. 3 shows the basic structure of a SAW RFID biosensor with selectable binary modulated finger electrodes within the IDT array. The biosensor of FIG. 3 is similar to the RFID biosensor of FIG. 2 with multiple reflective arrays 200 in that an antenna 320 receives an interrogation signal which is converted to an acoustic wave #1 342 by the input/output IDT 315. This binary modulation includes a variety of coding schemes such as, but not limited to, binary codes, Barker codes, combined Barker codes, Gold codes, quadraphase codes and pseudorandom (PN) codes. The electrical connections of the antenna 320 extend past the input/output IDT 315 by means of conductive busbars 318. The antenna 320 excites the IDT array 316 which then propagates an acoustic wave #2 344 towards the input/output IDT 315. A binary modulated bit pattern is embedded into the finger pattern of the IDT array 316.

In the embodiment shown in FIG. 3, bit #1 371 is the input/output IDT which is made up of 3 finger electrode pairs and has a weighted binary value of 1. Bit #2 373 and bit #3 375 are made up of 3 finger electrode pairs and has a weighted binary value of 1. Bit #4 377 is also made up of 3 finger electrode pairs, but is phase reversed with respect to the other two bits, resulting in a weighted binary value of −1. A biolayer 335 is located within bit #4 377 and positioned so as to communicate with biological and chemical fluid entering a fluidic chamber inlet 362 and discharging through the fluidic chamber outlet 364. When the biolayer 335 interacts with specific biological and chemical substances, a change in velocity of the acoustic wave occurs within the piezoelectric material under the biolayer 335. This change in velocity then perturbs the acoustic wave propagating under bit #4 377 IDT array.

Previous literature by co-inventor Edmonson ("SAW Pulse Compression Using Combined Barker Codes," M. Eng Thesis in Electrical Engineering, McMaster University, Hamilton, Ontario, Canada, March 1989) has demonstrated the use of correlation techniques and sidelobe analysis for the detection of modulated signals using SAW devices. The manner in which a passive SAW RFID biosensor can detect a substance will now be explained by means of example. The SAW structure will be that as shown in FIG. 3. The binary weighted bit values are 1 1 1 −1, where a space equal to a bit period (Tc) is inserted between the first and second bits to represent the spatial separation shown in the structure of an RFID biosensor with selectable IDT arrays as in FIG. 3. For the first 6 steps of this example there is no binding of substances to the biolayer. Binding is present after step 7. The steps involved are:

1. An interrogation signal is received at the antenna 320 of the RFID biosensor.
2. IDT array 316 transforms the RF electrical interrogation signal to an equivalent acoustic wave.
3. The acoustic waves begin to propagate outwards from the IDT array 316 in both the right (R) direction 342 and in the left (L) direction 344.
4. As the acoustic waves 342, 344 propagate under each set of IDT fingers representing a bit value 371, 373, 375, 377, a summation of acoustic wave values occurs and the resultants are transformed back to RF electrical signals via the IDT array 316 and transmitted back to the interrogation unit via the antenna 320.
5. Table 1 illustrates the propagation of the acoustic wave, with each row number representing the number of time periods (nTc) which the acoustic wave has propagated. The upper 4 rows represent the sequential shift of the acoustic wave to the right and the bottom 4 rows represent the sequential shift of the acoustic wave to the left.
6. After 4 time periods, the acoustic wave has cleared the IDT array 316 in both directions and the summation values are shown in Table 2. These are the equivalent RF values which will be transmitted back to the main interrogation unit.

TABLE 1

| | | | | | | | | |
|---|---|---|---|---|---|---|---|---|
| 4R  | | | | | | 1 | 1 1 | −1 |
| 3R  | | | | | 1 | 1 1 | −1 | |
| 2R  | | | | 1 | 1 1 | −1 | | |
| 1R  | | | 1 | 1 1 | −1 | | | |
| IDT | | 1 | 1 1 | −1 | | | | |
| 1L  | 1 | 1 1 | −1 | | | | | |
| 2L  | 1 | 1 1 | −1 | | | | | |
| 3L  | 1 | 1 1 | −1 | | | | | |
| 4L  | 1 | 1 1 | −1 | | | | | |

TABLE 2

| | Rows 1 | Rows 2 | Rows 3 | Rows 4 |
|---|---|---|---|---|
| Summation | 0 | 0 | 2 | −2 |

7. The reminder of this example shows the situation where the biolayer 335 has been exposed to biological or chemical substances and a binding event has taken place.
8. Steps 1 through 4 are repeated except that the velocity has changed within the SAW structure under the biolayer located at bit #4 377. When a binding event takes place between the biological or chemical substances and the biolayer 335, a change in acoustic wave velocity under the biolayer 335 will occur. This velocity perturbation translates into a change in frequency, and the subsequent acoustic wave associated with bit #4 377 will propagate and transfer this change to each group of fingers within the IDT that the acoustic wave propagates through. Similarly, when an acoustic wave originating from an unperturbed set of IDTs 371, 373, 375 propagates through the IDT of bit #4 377, a velocity perturbation will also take place resulting in a frequency change.

9. Table 3 illustrates the resulting propagation of the acoustic wave and the perturbed value of bit #4 377 which arbitrarily shown as 0.9 rather than 1.0 to illustrate the binding effect. Even though a change caused by the biolayer is represented by a change in amplitude and not frequency, it can be shown that when the perturbed interrogation signal is returned back to the interrogation unit and undergoes a correlation process with a reference signal, the frequency change can be represented by an amplitude change within the resulting peak and sidelobe values.

TABLE 3

| | | | | | | | | | | | |
|---|---|---|---|---|---|---|---|---|---|---|---|
| 4R  |   |   |   |   |   |   |   | 1 |   | 1 | 1 | -0.9 |
| 3R  |   |   |   |   |   |   | 1 |   | 1 | 1 | -0.9 |
| 2R  |   |   |   |   |   | 1 |   | 1 | 1 | -0.9 |
| 1R  |   |   |   |   | 1 |   | 1 | 1 | -0.9 |
| IDT |   |   |   | 1 |   | 1 | 1 | -0.9 |
| 1L  |   |   | 1 |   | 1 | 1 | -0.9 |
| 2L  |   | 1 |   | 1 | 1 | -0.9 |
| 3L  | 1 |   | 1 | 1 | -0.9 |
| 4L  | 1 | 1 | -0.9 |

10. The resultant summation is shown in Table 4, illustrating the change in the summation values when compared to Table 2 for the unperturbed state. The main interrogation unit will decode a different set of summation peak and sidelobe values with respect to the unperturbed state when no binding occurred and determine if a detection sequence has occurred. The difference between the summation values of Tables 2 and 4 is proportional to the amount of substance detected.

TABLE 4

|  | Rows 1 | Rows 2 | Rows 3 | Rows 4 |
|---|---|---|---|---|
| Summation | 0.2 | 0.2 | 2 | -1.8 |

Figure 4:
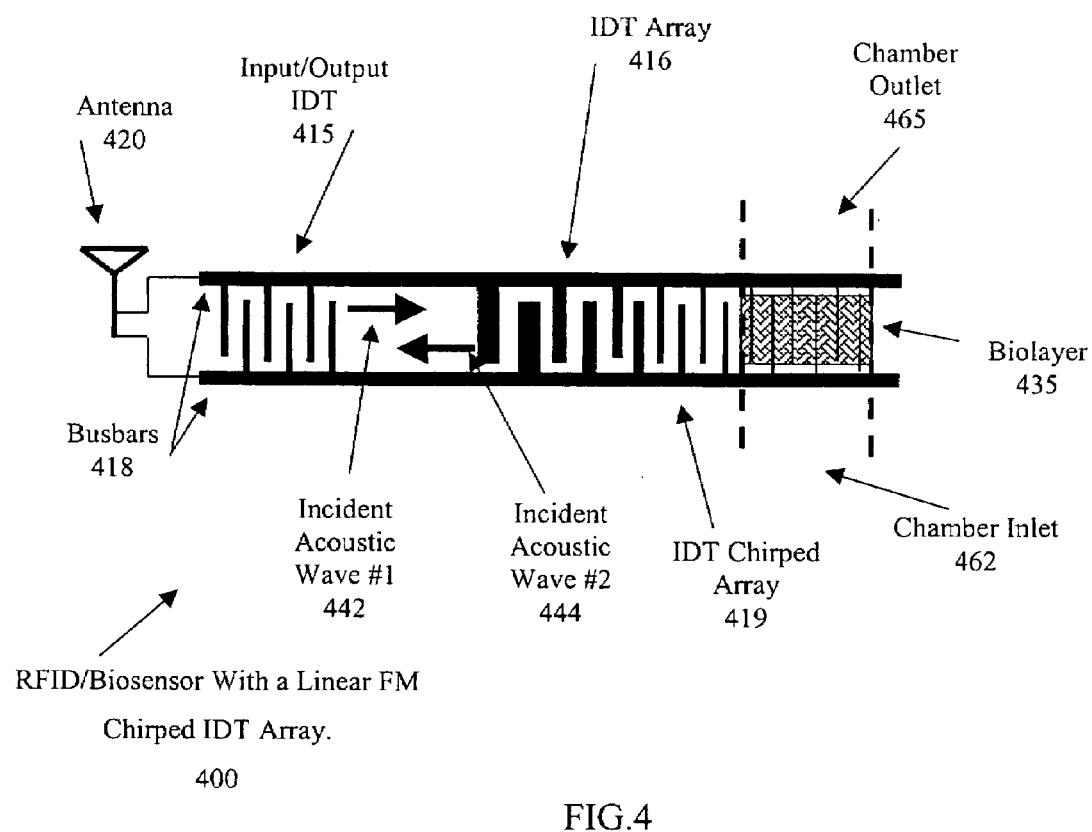
FIG. 4 is a similar view of an RFID biosensor with a linear FM chirped IDT array in accordance with a still further embodiment.

FIG. 4 illustrates another embodiment of the invention, namely a SAW RFID biosensor with a singly dispersive in-line frequency modulated (FM) chirp IDT array 400. An IDT array 416 is again separated into two main regions. This frequency modulation includes a variety of coding schemes such as, but not limited to, linear FM, non-linear FM, minimum shift keying (MSK) coding and Frank codes. An input/output IDT 415 occupies the left most region of the IDT array 416 and a chirped IDT 419 occupies the right most region. An antenna 420 receives an interrogation signal which is converted to an acoustic wave #1 442 by the input/output IDT 415. The electrical connections of the antenna 420 extend past the input/output IDT 415 by means of conductive busbars. The antenna 420 excites the IDT chirped array 419, which then propagates an acoustic wave #2 444 towards the input/output IDT 415.

The finger pattern of the chirped array 419 varies in width. Wide fingers represent lower frequencies and narrow fingers represent higher frequencies following the relationship $\lambda = v/f$, where $\lambda$ is the acoustic wavelength, $v$ is the acoustic velocity and $f$ is the frequency. Typically, each finger is $\lambda/4$ in width.

The RFID biosensor of FIG. 5 has a linear FM chirped IDT array with a linear modulated FM up-chirp finger pattern within the array 419. A biolayer 435 is located within the higher frequency fingers of the chirped array 419 and positioned such to communicate with biological and chemical fluid entering the fluidic chamber through an inlet 462 and discharging from an outlet 464. When the biolayer 435 interacts with specific biological and chemical substances, a change in velocity of the acoustic wave occurs within the piezoelectric material under the biolayer region 435. This change in velocity then perturbs the acoustic wave propagating under the higher frequency fingers of the chirped array 419.

With no binding of substances to the biolayer 435, the interrogation signal excites the IDT array 416 to produce an unperturbed return signal back to the interrogation unit such that the modulated frequency of the signal increases linearly from a low to high frequency component. When there is a binding event between the fluid and the biolayer 435, a perturbed returning signal back to the interrogation unit is produced such that the modulated frequency component of the signal is no longer linear due to the change in velocity occurring under the higher frequency fingers, thereby perturbing the frequency component of the signal. It can be shown that, when the perturbed interrogation signal is returned back to the interrogation unit and undergoes a correlation process with an equivalent matched filter such as a down-chirped reference signal, the frequency change can be represented by an amplitude change within the resulting peak and sidelobe values.

Other embodiments and advantages of the invention will now be readily apparent to a person skilled in the art, the scope of the invention being defined in the appended claims.

The invention claimed is:

1. A surface acoustic wave sensor or identification device having:
   a piezoelectric material,
   an interdigitated transducer (IDT) input/output mounted on the piezoelectric material for receiving a radio frequency (RF) signal and propagating a corresponding surface acoustic wave along a surface of the piezoelectric material,
   an IDT finger electrode array mounted on the piezoelectric material and operable to communicate with the IDT input/output for transmission of a modified RF signal from the device,
   said IDT finger electrode array having at least one finger electrode segment whose propagating characteristics are controlled to control the nature of the modified RF signal,
   a biolayer mounted on the piezoelectric material and associated with the finger electrode segment, and
   a fluidic chamber associated with the biolayer and which in use contains fluid which, if a predetermined substance to be sensed or detected is present, operates to modify the biolayer which in turn controls the nature of the modified RF signal.

2. A sensor or identification device according to claim 1 wherein the IDT finger electrode array comprises a reflector array.

3. A sensor or identification device according to claim 1 wherein the IDT finger electrode segment comprises a modulated IDT array.

4. A sensor or identification device according to claim 1 wherein the fluidic chamber has an inlet and an outlet whereby in use the fluid flows through the chamber from the inlet to the outlet.

5. A sensor or identification device according to claim 1 wherein said at least one finger electrode segment has at least one pair of interdigitated fingers which communicate with the fluidic chamber.

6. A sensor or identification device according to claim 5 wherein said at least one pair of interdigitated fingers project into the chamber.

7. A sensor or identification device according to claim 1 wherein the modified RF signal is detected within a detection algorithm located within the main interrogation unit.

8. A detection algorithm according to claim 7 wherein the modified RF signal is detected by comparison to a reference frequency.

9. A detection algorithm according to claim 7 wherein the modified RF signal is detected by comparison to a reference phase.

10. A detection algorithm according to claim 7 wherein the modified RF signal is detected by comparison to a reference modulation code.

* * * * *